United States Patent [19]
Murakami et al.

[11] 3,956,329
[45] May 11, 1976

[54] PROCESS FOR PREPARING NITROGEN-CONTAINING HETEROCYCLIC COMPOUNDS

[75] Inventors: Ryuzo Murakami; Shigeaki Kato; Hiroshi Mitarashi, all of Tokuyama, Japan

[73] Assignee: Shunan Petrochemical Company, Ltd., Tokyo, Japan

[22] Filed: July 19, 1974

[21] Appl. No.: 489,926

[30] Foreign Application Priority Data
July 19, 1973 Japan............................. 48-82278

[52] U.S. Cl............................ 260/268 SY; 260/217
[51] Int. Cl.² ........................................ C07D 295/02
[58] Field of Search .................. 260/268 T, 268 SY

[56] References Cited
UNITED STATES PATENTS

| | | | |
|---|---|---|---|
| 2,977,363 | 3/1961 | Farkas et al...................... | 260/268 T |
| 2,977,364 | 3/1961 | Mascioli .......................... | 260/268 T |
| 2,985,658 | 5/1961 | Krause ............................ | 260/268 T |
| 3,369,019 | 2/1968 | Hamilton et al. ................ | 260/268 T |
| 3,772,293 | 11/1973 | Oakes et al. .................... | 260/268 T |

Primary Examiner—Richard J. Gallagher
Assistant Examiner—Jose Tovar
Attorney, Agent, or Firm—Oblon, Fisher, Spivak, McClelland & Maier

[57] ABSTRACT

Nitrogen-containing heterocyclic compounds are prepared by cyclization of a compound having the formula:

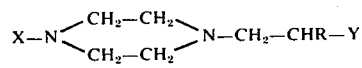

or

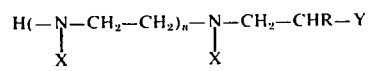

wherein X represents a hydrogen atom or —CH$_2$CHR-Y; R represents a hydrogen atom or methyl atom; Y represents an —OH group or —NH$_2$ group; and n represents the integers 0 or 1 - 4; with a zeolite catalyst having the formula

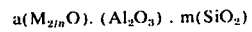

wherein M represents a cation selected from alkali metals, alkaline earth metals, zinc group elements, hydrogen and ammonium cations; $n$ represents the valence of the cation; a is $1.0 \pm 0.5$ and m is 2 - 12.

5 Claims, No Drawings

PROCESS FOR PREPARING NITROGEN-CONTAINING HETEROCYCLIC COMPOUNDS

BACKGROUND OF THE INVENTION

1. Field of the Invention

The present invention relates to a process for preparing nitrogen-containing heterocyclic compounds. More particularly, the invention relates to a process for preparing nitrogen-containing heterocyclic compounds, such as triethylenediamines, piperidines and morpholines by dehydrocyclization or cracking cyclization (deammoniation) of compounds having formulas (I) and (II) in the presence of a zeolite catalyst containing a specific cation.

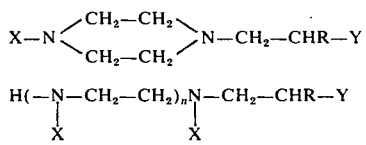

wherein X represents a hydrogen atom or $-CH_2-CHR-Y$ group; R represents a hydrogen atom or methyl group; Y represents an $-OH$ or $-NH_2$ group and n represents the integers 0 or 1 to 4.

2. Description of the Prior Art

Triethylenediamines have been prepared by cyclization of the above compounds (I and II) in the presence of a metal phosphate catalyst (Japanese Pat. Publication No. 18589/1966) or a silica-alumina catalyst (Japanese Pat. Publication No. 22597/1963; Japanese Pat. Publication No. 7707/1969).

A need exists, however, for a catalytic procedure for preparing a wide range of nitrogen heterocycles.

SUMMARY OF THE INVENTION

Accordingly, one object of the invention is to provide a catalytic process for preparing diverse nitrogen-containing heterocyclic compounds.

Another object of the invention is to provide a novel catalyst for preparing diverse nitrogen-containing heterocyclic compounds.

These and other objects as will hereinafter become more readily understood can be attained by a process for preparing nitrogen-containing heterocyclic compounds by the cracking cyclization reaction of

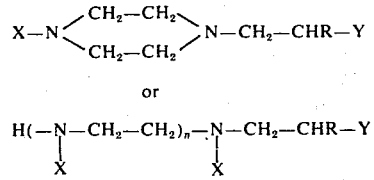

wherein X is hydrogen of $-CH_2-CH_2Y$, R is hydrogen or methyl, Y is $-OH$ or $-NH_2$ and n is the integer 0 or 1 to 4, over a zeolite catalyst of the formula $$a(M_{2/n}O) \cdot (Al_2O_3) \cdot m(SiO_2)$$

wherein M is at least one cation selected from the group of alkali metals, alkaline earth metals, zinc group elements, hydrogen and ammonium cations; n is the valence of the cation; a represents the number $1.0 \pm 0.5$ regardless of the type and number of cations and m represents the numbers of 2 - 12.

DETAILED DESCRIPTION OF THE PREFERRED EMBODIMENTS

The zeolite used for the catalyst of the invention is a macromolecular crystalline aluminosilicate having the formula $$a(M_{2/n}O) \cdot (Al_2O_3) \cdot m(SiO_2) \qquad \text{III}$$

wherein M represents a cation selected from alkali metals, alkaline earth metals, zinc group elements and hydrogen and ammonium cations; n represents the valence of the cation, a represents $1.0 \pm 0.5$ regardless of the type and number of the cation and m represents the numbers 2 - 12.

Natural and synthetic zeolites may be used. Typical synthetic zeolites include zeolite A, zeolite X and zeolite Y, which are commercially available as molecular sieves manufactured by Union Carbide Corp. (U.C.C.) Zeolites may be prepared from silicate and aluminte starting materials and treating the product with hot water.

Typical natural zeolites include:
gismondite $[CaO \cdot (Al_2O_3) \cdot 2(SiO_2) \cdot 4H_2O]$
natrolite $[Na_2O \cdot (Al_2O_3) \cdot 3(SiO_2) \cdot 2H_2O]$
chabazite $[(NaCa) \cdot O(Al_2O_3) \cdot 4(SiO_2) \cdot 6H_2O]$ and
harmotome $[BaO \cdot (Al_2O_3) \cdot 6(SiO_2) \cdot 6H_2O]$ When a zeolite is used as the catalyst, the water in the zeolite (crystallized water and adsorbed water) is removed by heating or by other methods.

The zeolites used in the invention have a crystal structure with specific spaced lattices which depend on the value of $m(SiO_2/Al_2O_3)$ and the type and number of cations M in formaula (III). Most cations can be easily exchanged with other cations without destroying the crystal structure having the spaced lattice.

The zeolite containing the desired cation may be easily prepared by ion exchange. For example, one method of ion exchange involves placing powdered or shaped zeolite containing Na, K or Ca cations in a cylinder equipped with a suitable holder, and an aqueous solution containing a salt with a desired cation for ion exchange is continuously passed through. Another method involves placing the zeolite and the aqueous solution of a salt in a reactor equipped with a reflux condenser, and heating or boiling the mixture. The resulting zeolite is washed with distilled water to remove the residual salt, and is then heated higher than 100°C to remove the water. Two or more kinds of cations may be exchanged in the zeolite by using an aqueous solution of a mixture of salts containing two or more types of cations. In general, an aqueous solution of hydrochloric acid is used for ion-exchanging hydrogen cations. An aqueous solution of a halide of lithium, calcium, magnesium, strontium or ammonium is used for ion-exchanging these cations. An aqueous solution of zinc nitrate is used for ion-exchanging zinc cation. The ion-exchange capacity is dependent upon the type of cation and the concentration of the salt, and may vary widely in the invention.

When zeolite is used as a catalyst, a zeolite having the formula (III), wherein the cation M is an alkaline earth metal or ammonium ion, is preferable, most preferably calcium or ammonium ion. The value of $m(SiO_2/Al_2O_3)$ is preferably 2 - 3. Synethetic zeolites, such as zeolite A and zeolite X and natural zeolites, such as sodalite and gismondite are examples of preferable catalysts included in the definition.

Suitable starting amine compounds shown by the formula (I) include

N($\beta$-aminoethyl)piperazine
N,N'-bis-($\beta$-aminoethyl)piperazine
N-$\beta$-hydroxyethyl)piperazine
N,N'-bis-($\beta$hydroxyethyl)piperazine
N-($\beta$-aminopropyl)piperazine
N-($\beta$-hydroxypropyl)piperazine, and
N,N'-bis-($\beta$-hydroxypropyl)piperazine.

These compounds may be prepared by reacting piperidine with ethyleneoxide, propyleneoxide, ethyleneimine or propyleneimine by conventional methods.

Suitable starting compounds shown by the formula (II) include ethylenediamine,
diethylenetriamine,
triethylenetetramine,
tetraethylenepentamine,
pentaethylenehexamine, and
mono- and diethanolamine, and also include compounds prepared by reacting these compounds with ethyleneoxide, propyleneoxide, ethyleneimine or propyleneimine, to produce, for example, triethanolamine, N-($\beta$-aminoethyl)diethanolamine,
N-($\beta$-hydroxypropyl)ethylenediamine,
N,N'-bis($\beta$-hydroxyethyl)ethylenediamine and
N,N'-tetra-($\beta$-hydroxyethyl)ethylenediamine.

In the reaction of the invention, the zeolite catalyst may be in the form of powder, granules, pellets, or cylindrical rings which can be formed using a clay binder. A reactor is filled with the catalyst and one or more kinds of starting material is contacted with the catalyst in the gas phase. The reaction temperature is usually 250° – 550°C, preferably 350° – 450°C. The pressure may be atmospheric pressure or reduced or high pressure.

The rate of feeding the starting material is preferably 0.01 – 3.0 g/g-cat. hr., most preferably 0.2 – 1.0 g/g-cat. hr. (g of the starting material per 1 g of catalyst for 1 hour). A carrier gas, such as ammonia and nitrogen may be used together with the starting material. The reaction may be carried out in a fixed bed or a fluidized bed reactor. The size and shape of the catalyst used in the fixed bed reaction, may vary and is usually spherically shaped having a diameter of about 2 – 15 mm; or cylindrically shaped having a diameter of about 2 – 15 mm and length of about 2 – 15 mm.

Having generally described the invention, a further understanding can be obtained by certain specific examples which are provided herein for purposes of illustration only and are not intended to be limiting in any manner.

EXAMPLE 1

A zeolite A catalyst [CaO.(Al$_2$O$_3$).2(SiO$_2$)] having a cylindrical shape (3 mm diameter, 6 – 8 mesh) sold as molecular sieves (manufactured by U.C.C.) was used. A reactor having an inner diameter of three-quarter inch and having an outer heater was filled with the catalyst to form a catalyst bed with a length of 20 cm. The starting material, N-($\beta$-aminoethyl)piperazine, which was preheated to about the reaction temperature was fed at a rate of 0.63 g/g-cat. hr. to the reactor at 390°C under atmospheric pressure, whereby cracking cyclization was performed. The reaction mixture was collected by cooling with water and the reaction products were analyzed by quantitative gas chromatography. Ammonia was absorbed in dilute sulfuric acid and the residual unabsorbed waste gas was quantitatively measured with a gas meter. According to the analysis, the following results were obtained.

| | |
|---|---|
| Rate of cracking of starting material | 37.0% |
| Reaction products: | |
| triethylenediamine | 37.2% |
| piperazine | 32.0% |
| other amines | 12.7% |
| ammonia | 10.3% |
| waste gas | 7.8% |

EXAMPLE 2

The process of Example 1 was repeated except that N-($\beta$-hydroxyethyl) piperazine was fed at a rate of 0.81 g/g-cat. hr., to perform the dehydrocyclization. The results are as follows. The water content in the product was measured by the Karl Fischer method.

| | |
|---|---|
| Rate of cracking of starting material | 91.7% |
| Reaction products: | |
| teiethylenediamine | 54.8% |
| piperazine | 12.7% |
| other amines | 16.0% |
| ammonia | trace |
| water | 13.5% |
| waste gas | 3.0% |

EXAMPLES 3 – 12

Zeolite containing various cations (M$_{2/n}$O.Al$_2$O$_3$.SiO$_2$ type) and having a cylindrical shape (3 mm diameter, 6 – 8 mesh) was placed in the reactor of Example 1 (catalyst bed having a length of 20 cm). The starting material N-($\beta$-aminoethyl)piperazine, was fed at a rate of 0.49 g/g -cat. hr. and nitrogen (carrier gas) was fed at a rate of 0.38 l/g-cat. hr. at 390°C under atmospheric pressure, whereby a cracking cyclization reaction was performed. The results are shown in Table 1. The zeolite was prepared by ion-exchange of H, Ca, NH$_4$, Ba, Mg, Zn, or the like.

In the ion-exchange method, 0.1 N–HCl was continuously passed through the zeolite layer to give a pH of about 4 and to prepare a zeolite containing a hydrogen cation. Zeolites containing Ca, Ba, Mg, NH$_4$ or Zn were prepared by heating the original zeolite with aqueous solutions of 0.5 mole/l of CaCl$_2$, BaCl$_2$, MgCl$_2$, NH$_4$Cl or Zn(NO$_3$)$_2$ (1.5 molar ratio of cation to the cation of the zeolite) under reflux for 10 hours.

The zeolite obtained was washed with water and dried for use as the catalyst. The amount of cation exchanged by the ion-exchange method is not clear, however, the effects of the cation are clear from the results of Table 1. By comparison of Examples 4 to 7 with Examples 8 and 9, the beneficial effects of the exchanged cation may be clearly seen, even though the original zeolites are different.

TABLE 1

| | Cation in catalyst | | | Main reaction product | | |
|---|---|---|---|---|---|---|
| Example | original zedite | ion-exchange zedite | Amount of cracking (%) | triethyl-enediamine (%) | piperazine (%) | Other amines (%) |
| 3 | Na | | 75.2 | 27.4 | 36.1 | 11.7 |
| 4 | K | | 42.4 | 19.2 | 39.4 | 20.0 |
| 5 | Ca | | 90.5 | 38.5 | 32.3 | 11.3 |
| 6 | Na | H | 86.5 | 31.6 | 37.8 | 11.5 |
| 7 | K | Ca | 88.2 | 34.4 | 32.6 | 10.7 |
| 8 | Na | NH$_4$ | 97.4 | 39.7 | 27.8 | 8.9 |
| 9 | Ca | NH$_4$ | 97.1 | 41.0 | 31.2 | 8.3 |
| 10 | Na | Ba | 97.7 | 35.5 | 33.8 | 9.1 |
| 11 | Na | Mg | 89.3 | 35.0 | 34.6 | 10.7 |
| 12 | Na | Zn | 57.3 | 28.4 | 32.9 | 20.9 |

EXAMPLES 13 – 15

Zeolite A, X and Y catalysts manufactured by U.C.C. were used. The starting material, N-($\beta$-aminoethyl)piperazine, was fed over the catalysts at a rate of 0.40 g/g-cat. hr. without a carrier gas at 390°C under atmospheric pressure in accordance with the process of Example 3, whereby the cracking cyclization reaction was performed. The results are shown in Table 2.

TABLE 2

| | | | Amount | Main reaction product | | |
|---|---|---|---|---|---|---|
| Example | Type of zeolite (m value) | Type of cation | of cracking (%) | tri-ethylene diamine (%) | piperazine (%) | other amines (%) |
| 13 | zeolite A type (m=2) | Na | 83.4 | 32.3 | 34.5 | 14.6 |
| | | Ca | 91.5 | 37.5 | 31.0 | 10.2 |
| | | Na.NH$_4$ | 97.1 | 39.4 | 29.9 | 14.0 |
| 14 | zeolite X type (m=2.5) | Na | 65.3 | 24.8 | 35.0 | 23.5 |
| | | Ca | 99.8 | 30.8 | 20.3 | 23.0 |
| | | Na.NH$_4$ | 98.6 | 39.6 | 31.0 | 10.0 |
| 15 | zeolite Y type (m=3–6) | Na | 99.2 | 24.3 | 31.5 | 23.6 |
| | | Ca | 99.3 | 27.3 | 27.6 | 29.0 |
| | | Na.NH$_4$ | 81.6 | 28.5 | 29.8 | 22.8 |

EXAMPLES 16 – 18

The process of Example 1 was repeated except that the starting material, N-($\beta$-hydroxyethyl)piperazine was fed, or a mixture of 26 weight parts of N-($\beta$-hydroxyethyl)piperazine and 74 weight parts of N,N'-bis-($\beta$-hydroxypropyl)piperazine were fed to the catalyst at 390°C under atmospheric pressure to perform the cracking cyclization reaction. The results are shown in Table 3.

EXAMPLES 19 – 23

Zeolite A catalyst containing Ca or NH$_4$ cation was then placed in the reactor of Example 1 to form a catalyst bed having a length of 20 cm. Starting materials shown in Table 4, such as ethanolamine, or the like, were fed at a rate of 0.65 g/g-cat. hr. under atmospheric pressure at 384° – 388°C (ethylenediamine 330°C; ethanolamine 365°C) to perform the cyclization. The results are shown in Table 4. In Table 4, some starting materials with indicated concentrations such as tetraethylenepentamine and pentaethyl hexamine include ethylenepolyamines such as triaminoethylamine and N,N'-bis-($\beta$-aminoethyl)piperazine. The products marked with a * contain a methyl group at the 2-position of the carbon atom of the piperazine, morpholine and triethylenediamine.

TABLE 3

| Example | Starting material | Feed Rate of starting material g/g-cat. hr. | Amount of cracking (%) | Main reaction product | | | | |
|---|---|---|---|---|---|---|---|---|
| | | | | TEA (%) | MTEA (%) | PIP (%) | MPIP (%) | other amines (%) |
| 16 | N-($\beta$--hydroxyethyl) piperazine | 0.50 | 99.6 | 57.6 | — | 12.3 | — | 16.0 |
| | | | 98.3 | 61.6 | — | 14.3 | — | 9.0 |
| 17 | N-($\beta$-hydroxypropyl piperazine | 0.54 | 95.9 | — | 36.0 | 22.5 | 4.9 | 21.9 |
| 18 | N-($\beta$-hydroxypropyl) piperazine + N'N-bis-($\beta$-hydroxy- | 0.49 | 90.8 | — | 33.0 | 23.9 | 4.9 | 24.2 |

TABLE 3-continued

| Example | Starting material | Feed Rate of starting material g/g-cat. hr. | Amount of cracking (%) | Main reaction product |||| other amines (%) |
|---|---|---|---|---|---|---|---|---|
| | | | | TEA (%) | MTEA (%) | PIP (%) | MPIP (%) | |
| | propyl) piperazine | | | | | | | |

TEA: triethylenediamine
MTEA: 2-methyltriethylenediamine
PI: piperazine
MPIP: 2-methyl piperazine

Table 4

| Example | Starting material | Type of cracking catation | Amount of cracking (%) | Main reaction product |||| other amines (%) |
|---|---|---|---|---|---|---|---|---|
| | | | | TEA (%) | PI (%) | API (%) | HPI (%) | |
| | | NH$_4$ | 82.4 | 15.1 | 13.0 | 10.9 | 1.9 | 19.7 |
| | | NH$_4$ | 98.9 | 20.6 | 3.6 | 3.9 | 1.9 | 14.0 |
| | | NH$_4$ | 87.1 | 10.0 | 7.4 | 1.2 | 3.5 | 20.8 |
| 19 | ethylenediamine | Ca | 19.3 | 15.3 | 24.4 | 16.8 | — | 27.6 |
| 20 | diethylenetriamine | Ca | 100 | 17.8 | 25.2 | 6.0 | — | 23.8 |
| 21 | triethylenetetramine | Ca | 99.6 | 22.6 | 21.7 | 9.3 | — | 22.8 |
| 22 | 75%-tetraethylenepentamine | NH$_4$ | 99.7 | 21.7 | 24.5 | 4.9 | — | 28.8 |
| 23 | 65%-pentaethylenehexamine | Ca | 98.9 | 17.8 | 22.5 | 11.8 | — | 31.8 |
| | | NH$_4$ | 97.2 | 16.4 | 4.2 | 0.5 | 2.1 | 30.4 |

TEA: triethylenediamine
PI: piperazine
API: N-(β-aminoethyl)piperazine
HPI: N-(β-hydroxyethyl)piperazine

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. In a process for preparing a nitrogen-containing heterocyclic compound by cracking cyclization of a compound of the formula:

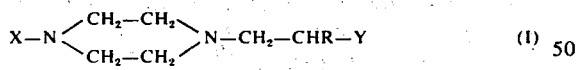    (I)

or

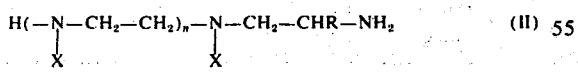    (II)

wherein
X represents hydrogen or —CH$_2$—CHR—Y;
R represents hydrogen or methyl;
Y represents an —NH$_2$ group; and
n represents the integers 0 or 1 – 4;
the improvement which comprises the step of:
cracking said compound I or II over zeolite catalyst having the formula:

$a(M_{2/n}O)\cdot(Al_2O_3)\cdot m(SiO_2)$    (III)

wherein M represents at least one cation selected from the group consisting of alkali metals, alkaline earth metals, zinc group elements, hydrogen and ammonium cations; n represents the valence of the cation; a represents the number of 1.0 ± 0.5, regardless of the type and number of cations and m represents the numbers of 2 – 12.

2. The process of Claim 1, wherein said compound (I) or (II) is selected from the group consisting of
N-(β-aminoethyl)piperazine
N,N'-bis(β-aminoethyl)piperazine
N-(β-hydroxyethyl)piperazine
N,N'-bis(β-hydroxyethyl)piperazine
N-(β-aminopropyl)piperazine
N-(β-hydroxypropyl)piperazine
N,N'-bis(β-hydroxypropyl)piperazine
ethylenediamine
diethylenediamine
triethylenetetramine
tetraethylenepentamine
pentaethylenehexamine.

3. The process of claim 1, wherein said zeolite catalyst has the formula $a(M_{2/n}O)\cdot(Al_2O_3)$ 2 – 3 $(SiO_2)$ wherein M represents an alkaline earth metal or ammonium ion and a represents 1.0 ± 0.5.

4. The process of claim 3, wherein M is Ca or NH$_4$.

5. The process of claim 1, wherein the cyclization reaction is conducted at 250°– 550°C by feeding the starting material at a rate of 0.01 – 3.0 g/g-cat. hr.

* * * * *